United States Patent [19]
Frank et al.

[11] 4,301,140
[45] Nov. 17, 1981

[54] RADIOPHARMACEUTICAL METHOD FOR MONITORING KIDNEYS

[75] Inventors: Patricia Frank, Evanston; Stephen Kraychy, Northbrook; Ernest F. Le Von, Evanston, all of Ill.

[73] Assignee: G. D. Searle & Co., Chicago, Ill.

[21] Appl. No.: 103,822

[22] Filed: Dec. 14, 1979

[51] Int. Cl.$^3$ ............... A61K 49/00; A61K 43/00; G01T 1/00
[52] U.S. Cl. ............................ 424/1.5; 424/9; 424/285; 260/346.11; 260/429 J; 250/303
[58] Field of Search .............. 424/1, 1.5, 9, 278, 424/285, 361; 260/429 J, 346.11; 250/303

[56] References Cited
U.S. PATENT DOCUMENTS

| | | | |
|---|---|---|---|
| 3,749,913 | 7/1973 | Halpern et al. | 424/1 |
| 4,027,005 | 5/1977 | Adler et al. | 424/1.5 |
| 4,118,468 | 10/1978 | Strecker et al. | 424/1 |

OTHER PUBLICATIONS

Basmadjian et al., "Nuclear Medicine: State of the Art and Future", Proc. 15th Int. Ann. Meeting of the Soc. Nucl. Med., Gronigen, Netherlands, Sep. 13–16, 1977, publ. 1978.
Basmadjian, 1st Ann. Meeting on General Radio pharmaceutical Science, Atlanta, Ga. Jan. 22, 1978, Abstract of Oral Presentation.

Primary Examiner—Benjamin R. Padgett
Assistant Examiner—Christine M. Nucker
Attorney, Agent, or Firm—James R. Henes; James G. Passe

[57] ABSTRACT

Complexes of technetium-99m with fructose 6-phosphate or fructose 1,6-diphosphate or salts thereof having utility as radiopharmaceutical agents for monitoring the activity of an organ, their preparation and a method employing such complexes for externally monitoring the activity of an organ are disclosed.

4 Claims, 4 Drawing Figures

RADIOPHARMACEUTICAL METHOD FOR MONITORING KIDNEYS

BACKGROUND OF THE INVENTION

1. Field of the Invention

This invention relates generally to a radiopharmaceutical method and more particularly concerns the use of complexes of technetium-99m and fructose 6-phosphate or fructose 1,6-diphosphate or salts thereof in a process for externally monitoring the kidneys.

2. Description of the Prior Art

Studies of mammalian kidneys by means of the administration of a radiopharmaceutical agent generally involve external visualization or imaging of the kidneys and/or measurement of the clearance of the radiopharmaceutical agent from plasma through the renal system, measurement of the glomerular filtration rate alone of the agent through the kidneys, or measurement of the total renal function—that is, effective renal plasma flow—as the excretion of the agent by both glomerular filtration and renal tubule secretion. In general, if an intravenously administered radiopharmaceutical agent is excreted at least to a significant extent via the kidneys, the agent can be used to image the kidneys. Moreover, if an intravenously administered radiopharmaceutical agent is excreted solely by the kidneys and is cleared from the plasma in a short half-time, then the agent does not bind to any part of the kidneys and can be used to measure effectively renal plasma clearance and, if the agent is not acted upon by the renal tubules, also the glomerular filtration rate. However, if these same conditions are met except that the agent is acted upon by the renal tubules, then the agent can still be used to image the kidneys but only effective renal plasma clearance can be measured.

A determination of whether or not an intravenously administered radiopharmaceutical agent is excreted solely through the kidneys can be made from the rate of disappearance of an intravenously administered radiopharmaceutical agent from the plasma. The rate of disappearance of an intravenously administered radiopharmaceutical agent from the plasma is related to both its distribution throughout the body and its elimination from the body. An analysis of the clearance, or rate of disappearance, of the radiopharmaceutical agent from the plasma—which can be represented by a plot of the logarithm of the experimentally measured radiopharmaceutical activity in the plasma as the ordinate versus time after administration as the abscissa—can define the number and sizes of the individual compartments of distribution of the radiopharmaceutical agent within the body. Since the clearance of the radiopharmaceutical agent from each compartment to the next is an exponential function, the individual components of the experimentally measured plasma clearance curve can be identified by a process of curve peeling. This process of curve peeling or stripping can be performed manually or by means of computer programs such as CSTRIP and NONLIN. A. J. Stedman and J. G. Wagner, Journal of Pharmaceutical Sciences, Vol. 65, No. 7, July 1976, pp. 1006–1010; C. M. Metzler, G. L. Elfing and A. J. McEwen, Biometrics, Vol. 30, No. 3, Sept. 1974.

The terminal slope of the clearance curve represents the renal component after equilibration in all the compartments, if the kidneys are the only ultimate exit from the first compartment (plasma being part of the first volume). By the process of curve stripping, the other exponential functions can be identified. This is done manually by extrapolating the terminal linear portion back to the ordinate and subtracting this extrapolated line from the original curve to obtain a new set of points. A new curve or straight line most closely approximating these new points is thereby identified, again having a terminal linear portion that defines another slope corresponding to a second compartment of distribution. This process of curve stripping is continued until arriving at a final exponential function, that is, until the points obtained as the difference between a curve and its extrapolated terminal linear portion are most closely approximated by a straight line. The number of exponential functions defines the number of individual compartments or volumes of distribution, and their sum defines the total plasma clearance curve. In the alternative this operation can be performed using a computer with available computer programs.

A two-compartment model predicts that a plot of the logarithm of radiopharmaceutical activity in either compartment (in the case of renal function, (1) in the plasma or whole blood or (2) in the renal system) versus time after administration is represented by the sum of two exponential functions. Fitting the sums of the exponential functions to plots of the logarithm of observed radiopharmaceutical activity in a compartment versus time permits the determination of transfer constants and compartmental values. Deviation of such constants and values, and hence of the measured clearance curves, from corresponding constants, values and clearance curves, respectively, for normally functioning kidneys permits diagnosis of renal ailments. If such a semi-quantitative analysis of the clearance through the kidneys can be made the radiopharmaceutical agent can be used not only to externally image the kidneys but also to assess renal function.

The conventional radiopharmaceutical agent for external imaging of the kidneys and assessment of renal function is a complex of ortho-iodohippurate with the radionuclide iodine-131. The $^{131}$I-o-iodohippurate complex is particularly well suited for this purpose because it is excreted through the kidneys exclusively, not through the liver or through both the liver and the kidneys. Due to its exceptionally high organ specificity, $^{131}$I-o-iodohippurate appears to follow the two-compartment model for organ function assessment radiopharmaceutical agents. After intravenous injection, $^{131}$I-o-iodohippurate is cleared from the blood, concentrated in the urine and excreted into the urinary bladder.

However, $^{131}$I-o-iodohippurate suffers the disadvantage of containing the iodine-131 radionuclide which emits gamma rays having the relatively high energy of 0.364 MeV, thereby imposing a relatively low limit on the maximum permissible administration dosage of $^{131}$I-o-iodohippurate. Further the 8 day half-life of the iodine-131 radionuclide results in an excessive residual radiation dose following administration of millicurie quantities of $^{131}$I-o-iodohippurate and performance of the test. This residual radiation is a disadvantage per se and also necessitates that successive radiopharmaceutical tests be spaced by a sufficient number of days after administration of $^{131}$I-o-iodohippurate to permit the background radiation to decay to a sufficiently low level.

The radionuclide technetium-99m has a shorter half life and emits lower energy gamma rays that iodine-131 and would be preferred in complexes with o-iodohippurate. However, o-iodohippurate does not complex satisfactorily with technetium-99m.

Basmadjian et al., "Chemistry of Technetium Phosphate and Phosphonate Complexes: Applications to radiopharmaceuticals," in Nuclear Medicine: State of the Art and Future from the Proceedings of the 15th International Annual Meeting of the Society of Nuclear Medicine in Gronigen, Netherlands on Sept. 13-16, 1977, published in 1978., a report on organ-specific radiopharmaceuticals, disclose that organic compounds with the following phosphonate structures have been shown to complex technetium when the latter is reduced with stannous ions: $R-OPO_3H_2$, $R-CH_2-PO_3H_2$ and $R-NH-PO_3H_2$. The article points out that in-vivo biodistribution in rabbits indicates that localization of such complexes is governed by the side chain. Although the phosphate group is needed for the chelation of reduced technetium when it is present in the free ionized form, or esterified with alkyl groups, it does not influence in-vivo biodistribution.

Structure-biodistribution relationships show that when the R-group in the above structures is a $CH_3-$, $CH_3CH_2-$, $HOOCCH_2-$, $NH_2CH_2-$, etc, uptake of the complex in the bones is evident. However, as the chain length is increased, bone uptake is decreased with non-specific biodistribution evident. Furthermore, when the alkyl radical is anywhere from 2 to 5 carbon atoms in length, or when an aryl radical exists, no matter what other functional groups are present in the molecule, a complex "mainly" excreted by the kidneys is obtained. Basmadjian et al. also disclose that, in the case of organic esters of the orthophosphate moiety, of the structure $R-OPO_3H_2$ where R is alkyl or aryl, the technetium complex is "mainly" execreted by the kidneys, with a long half-time in the blood, and assert that this behavior indicates some kind of protein binding. Furthermore, Basmadjian, in an oral presentation entitled "Chemistry and Biodistribution of Technetium Phosphate Complexes," presented at the First Annual Meeting on General Radiopharmaceutical Science sponsored by the Radiopharmaceutical Science Council of the Society of Nuclear Medicine in Atlanta, Ga. on Jan. 22, 1978, disclosed that technetium-labelled complexes of glucose 6-phosphate and of fructose 1,6-diphosphate have been studied as bone-specific radiopharmaceutical agents.

However, the Basmadjian et al. and Basmadjian reports do not disclose the technetium-labelled complexes of organic esters of the orthophosphate moiety are excreted solely by the kidneys, but only disclose that such materials are excreted "mainly" by the kidneys. Moreover, such reports indicate that technetium complexes of organic esters of orthophosphate have a long half-time in the blood which indicates some kind of protein binding. However, such binding would prevent a radiopharmaceutical agent from being used to measure effective renal plasma clearance or glomerular filtration rate.

SUMMARY OF THE INVENTION

It is therefore a general object of the present invention to provide a radiopharmaceutical agent which meets the aforementioned requirements and solves the aforementioned problems.

More particularly, it is an object of this invention to provide a radiopharmaceutical agent which emits gamma rays of a simple spectrum and with an energy sufficiently low to permit effective collimation and efficient detection and with a half-life sufficiently short to permit the administration of millicurie quantities to a patient without an excessive post-test background radiation and which is sufficiently stable in vivo to permit effective imaging.

Another object is to provide a radiopharmaceutical agent which is excreted essentially exclusively via the renal system.

Similarly an object of the present invention is to provide a method of externally monitoring the kidneys which includes the intravenous administration of a solution containing the highly renal-selective radiopharmaceutical diagnostic agent of this invention.

Other objects and advantages of this invention will become apparent upon reading the following detailed description and appended claims and upon reference to the accompanying drawings.

These objects are achieved by the present invention which comprises a method of externally monitoring the renal system by intravenously administering a solution containing a complex of technetium-99m and a complexing agent of formula I or a pharmaceutically acceptable salt thereof, and radiochemically monitoring the distribution of the complex in the body of the patient.

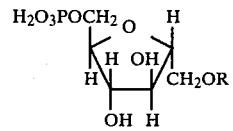

In formula (I), R is $-H$ or $-PO_3H_2$.

BRIEF DESCRIPTION OF THE DRAWINGS

For a more complete understanding of the invention, reference should now be made to the embodiments described below by way of examples of the invention and to the experimental results illustrated in the accompanying drawings and described below.

DETAILED DESCRIPTION

Figure 1:
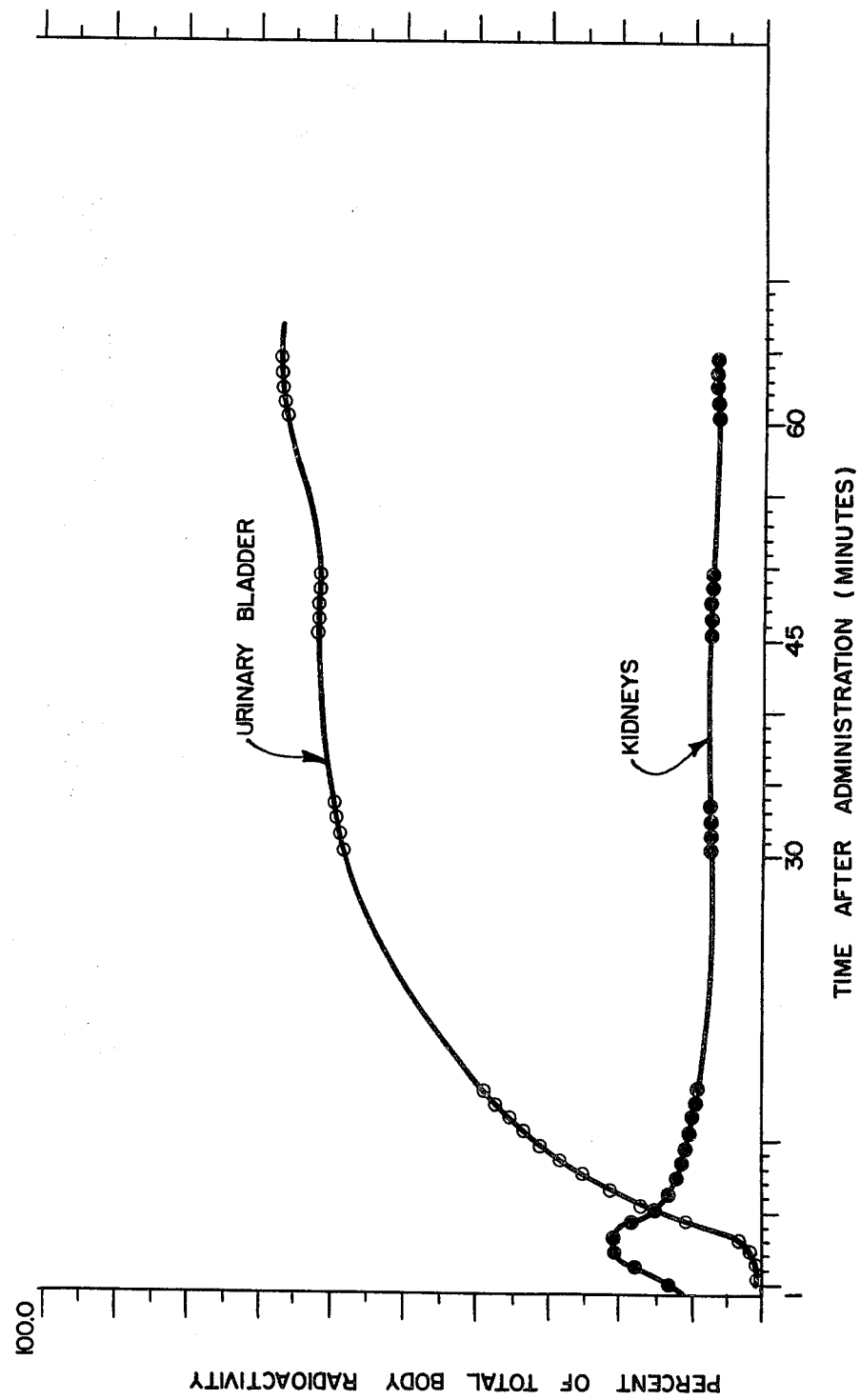
FIG. 1 contains plots of measured radioactivity found in the kidneys and urinary bladder of a dog as a percentage of total radioactivity of a complex of technetium-99/tin and fructose 6-phosphate administered intravenously to the dog versus time after administration.

The present invention is a method for externally monitoring the kidneys comprising administering intravenously a solution containing a complex of technetium-99m and of a complexing agent having formula I or a pharmaceutically acceptable salt thereof, and externally monitoring radiochemically its passage through the kidneys.

Suitable complexing agents include fructose 6-phosphate and fructose 1,6-diphosphate or their pharmaceutically acceptable salts. A suitable salt must be soluble in the solution to be administered intravenously. When the agent is a metal salt of a compound of formula I, the metal is suitably a metal such as lithium, sodium, potassium, rubidium, cesium, calcium, magnesium, zinc or cadmium. In the alternative, the complexing agent may be a salt of a compound of formula I and of a cationic material such as a quaternary ammonium ion, for example, tetracyclohexylammonium ion.

In preferred embodiments of the method of the present invention, R is also preferably $-PO_3H_2$.

When the complexing agent is a metal salt, the metal is preferably sodium. In the most preferred embodiment of the present invention, the method employs a complex of technetium-99m and fructose 1,6-diphosphate.

The complexes employed in the method of this invention can be prepared by any suitable conventional method from the aforementioned radionuclide and complexing agents of formula I or their pharmaceutically acceptable salts which are commerically available. It is preferred to admix the required amount of radionuclide and the appropriate amount of complexing agent, either in the form of the acid or salt, in aqueous solution at a pH of from about 2 to 7 and then adjusting the pH of the resulting solution to about 5 to 8 either with dilute sodium hydroxide or dilute hydrochloric acid as required. Technetium-99m is commercially available either from an isotope generator as a daughter of molybdenum-99 or as a direct product from a commercial supplier. It is also available as a solvent extraction product from molybdenum-99 solutions generally as alkaline metal pertechnetate solution at 5–100 millicuries per milliliter. A further discussion of preparative methods therefor appears in U.S. Pat. Nos. 3,468,808 and 3,382,152.

Preferably, the technetium-99m complex is prepared by reducing a solution of a pertechnetate, for example, an alkali metal pertechnetate, in the presence of a complexing agent. The pertechnetate reduction is effected utilizing any suitable reducing agent, including stannous chloride or other stannous salts such as stannous acetate, stannous tartrate or stannous oxalate, as well as cuprous salts or ferrous salts. As a result of this reduction step, the product may contain a significant proportion of a complex of the metal of the reducing agent, for example, the tin complex. It is to be understood that the complex used in the method of the present invention includes the product mixture containing both the complex of the radionuclide and, if used, the complex of the metal of the reducing agent.

The composition of this invention is most conveniently provided as a sterile kit consisting of non-radioactive chemicals for mixing with a radiometal source prior to use. The kit may contain the complexing agent in dry form or a solution of the complexing agent, as well as a pH buffer solution, or a combination thereof, and a solution of a suitable reducing agent. Using sterile reagents and aseptic techniques, the respective solutions can be mixed with each other and then with the radiometal source solution. The particular order of mixing is not critical. For example, a stannous salt solution can be added to the pertechnetate solution and the mixture combined with a solution of the complexing agent. Alternatively, a solution of the complexing agent can be combined with the pertechnetate solution prior to the addition of the stannous salt or it could be combined with the stannous salt and admixed with the pertechnetate. The resulting solution containing radiometal complex, excess complexing agent and, if a chemical reduction step is involved, a complex of the metal of the reducing agent, may then be employed directly.

The utility of the complexes of the method of this invention as radiopharmaceutical agents is evident from the following test procedures.

Approximately 0.2 milliliter of a solution of the complex formed from technetium-99m and 0.95 milligram of fructose 1,6-diphosphate and prepared generally as described in Example 1 and having a radioactivity of 0.5 millicurie was administered intravenously to an anesthetized New Zealand rabbit weighing about 3 kilograms. Approximately the same volume of a solution of the complex formed from technetium-99m and 1.21 milligrams of fructose 6-phosphate prepared generally as described in Example 2, having a radioactivity of 0.81 millicurie was similarly administered to a second New Zealand rabbit of about the same weight. The injections were made using a 1 milliliter tuberculin syringe connected to a #23 gauge indwelling cannula inserted into a marginal ear vein. Each rabbit was positioned in a full ventral position for 2.5 to 3 hours during which time the disposition of the radioactivity in the rabbit in this position was monitored using a computer-augmented Anger camera. The measurements and results are discussed hereinafter, and the results of the test using the fructose 1,6-diphosphate and fructose 6-phosphate complexes are presented in Tables 1 and 2, respectively.

TABLE 1

| Minutes After Administration | Relative distribution of Complex | | |
|---|---|---|---|
| | Vascular | Kidneys | Urinary Bladder |
| 1 | ++ | + | + |
| 3 | ++ | + | + |
| 30 | + | ++ | ++ |
| 60 | − | ++ | +++ |
| 180 | − | + | +++ |

TABLE 2

| Minutes After Administration | Relative Distribution of Complex | | |
|---|---|---|---|
| | Vascular | Kidneys | Urinary Bladder |
| 1 | ++ | ++ | + |
| 30 | + | ++ | ++ |
| 60 | + | ++ | +++ |
| 120 | − | + | +++ |
| 150 | − | + | +++ |

This procedure used with the rabbits was repeated with additional anesthetized animals: two female beagle dogs and two female rhesus monkeys. In these cases, however, unlike the cases of the rabbits, the complex solutions, again prepared generally as described in Examples 1 and 2, were injected intravenously in a saphenous vein of the dogs and monkeys.

Three milliliters of a solution of the complex formed from technetium-99m and 9.4 milligrams of fructose 1,6-diphosphate and having a radioactivity of 0.5 mCi were administered to one such dog weighing 11.7 kilograms. In addition, 1.6 milliliters of a solution of the complex formed from technetium-99m and 7.3 milligrams of fructose 6-phosphate having a radioactivity of 0.84 mCi were administered to a second such dog weighing 10.5 kilograms. Results of these tests with the first and second such dogs are presented in Tables 3 and 4, respectively.

Similarly 0.3 milliliter of a solution of the complex formed from technetium-99m and 1.1 milligrams of fructose 1,6-diphosphate having a radioactivity of 1.2 mCi were administered to one such monkey weighing 5.1 kilograms. Also 1.5 milliliters of a solution of the complex formed from technetium-99m and 7.6 milligrams of fructose 6-phosphate having a radioactivity of 0.79 mCi were administered to a second such monkey weighing 6.7 kilograms. Results of these tests with the first and second such monkeys are presented in Tables 5 and 6, respectively.

TABLE 3

| Minutes After Administration | Relative Distribution of Complex | | |
| --- | --- | --- | --- |
| | Vascular | Kidneys | Urinary Bladder |
| 5 | + | ++ | + |
| 13 | + | + | ++ |
| 40 | − | + | +++ |
| 60 | − | + | +++ |

TABLE 4

| Minutes After Administration | Relative Distribution of Complex | | |
| --- | --- | --- | --- |
| | Vascular | Kidneys | Urinary Bladder |
| 1 | ++ | ++ | − |
| 6 | + | ++ | + |
| 25 | + | + | ++ |
| 30 | + | + | +++ |
| 40 | − | + | +++ |
| 50 | − | + | +++ |
| 60 | − | + | +++ |
| 70 | − | + | +++ |
| 80 | − | + | +++ |
| 90 | − | + | +++ |

TABLE 5

| Minutes After Administration | Relative Distribution of Complex | | |
| --- | --- | --- | --- |
| | Vascular | Kidneys | Urinary Bladder |
| 6 | ++ | ++ | ++ |
| 16 | + | ++ | ++ |
| 27 | + | ++ | ++ |
| 36 | + | ++ | +++ |
| 46 | − | ++ | +++ |
| 56 | − | + | +++ |
| 70 | − | + | +++ |

TABLE 6

| Minutes After Administration | Relative Distribution of Complex | | |
| --- | --- | --- | --- |
| | Vascular | Kidneys | Urinary Bladder |
| 4 | + | ++ | +++ |
| 30 | + | ++ | +++ |
| 50 | − | + | +++ |
| 65 | − | + | +++ |

At various times after the aforesaid administrations of solutions of complexes of this invention, which times are indicated in Tables 1-6, scintiscan photographs and video tape recordings were taken of the aforesaid rabbit, beagles and monkeys using the Anger camera. This instrument was a Pho-Gamma LFOV Scintillation Camera System, Model 6413, fitted with a Model 3137 Vari-Back Camera, a Model 3122 Data-Store/Playback System and a Model 27851 Analog-Digital/Digital-Analog Converter (all Searle Radiographics, Inc.). This entire system was interfaced with a Xerox 530 computer (Xerox Corp., Minneapolis, Minn.) which was programmed to record net counts per unit of time and percents of total counts in individual organs and to plot organ radioactivity versus time. The camera was operated with a 140 KeV high resolution Type II converging collimator using a 20 percent technetium-99m window. Generally 400,000 counts were accumulated on each scintiscan using both video tape and self-developing film, with the animal in the full ventral position. The photographs represented a visualization of the anatomic relationships in the kidneys.

Tables 1-6 contain semi-quantitative representations of the distribution of radioactivity in the organs of the test animals determined from the scintiscans. In Tables 1-6, (−), (+), (++) and (+++) indicate relative amounts of measured radioactivity ranging from (−) for no significant measured radioactivity to (+++) for the maximum measured radioactivity.

Referring to Tables 1-2, there was extensive distribution of radioactivity throughout the vascular system of each rabbit with the heart, aorta and kidneys radioactive within one minute after administration of the complex of this invention. The complex was rapidly cleared from the circulatory system by the kidneys and within 1 to 3 minutes after administration of the complex to each rabbit, the complex appeared in the urinary bladder. Within 60 to 120 minutes after administration, no measurable radioactivity remained in the cardiovascular system, a relatively small amount remained in the kidneys, and the bulk of the complex was in the urinary bladder. Clearance of the complex from the vascular system appeared to be effected solely by renal elimination.

Turning to Tables 3-6, the distribution of the radioactive complex in the organs of the female beagles and monkeys is similar to that in the organs of the rabbits, and clearance from the vascular system in the female beagles and monkeys was also effected exclusively by renal excretion.

The appearance in the kidneys and urinary bladder of a male mongrel dog weighing 14.1 kilograms, of the radioactive complex formed from technetium-99m and 3-5 milligrams of fructose 6-phosphate administered intravenously as described above in a 0.5-1.0 milliliter solution prepared as in Example 2 and having a radioactivity of 3.5 mCi, was calculated from video tape measurements by the computer and is plotted in FIG. 1 as the percentage of total radioactivity administered in the form of the radioactive complex versus time after administration. At about 45 minutes after administration, about 60 percent of the total radioactivity administered was concentrated in the urinary bladder, with less than 7 percent of the total dose of the radioactive complex in the kidneys. No measurable radioactivity was concentrated in any other organ.

Figure 2:
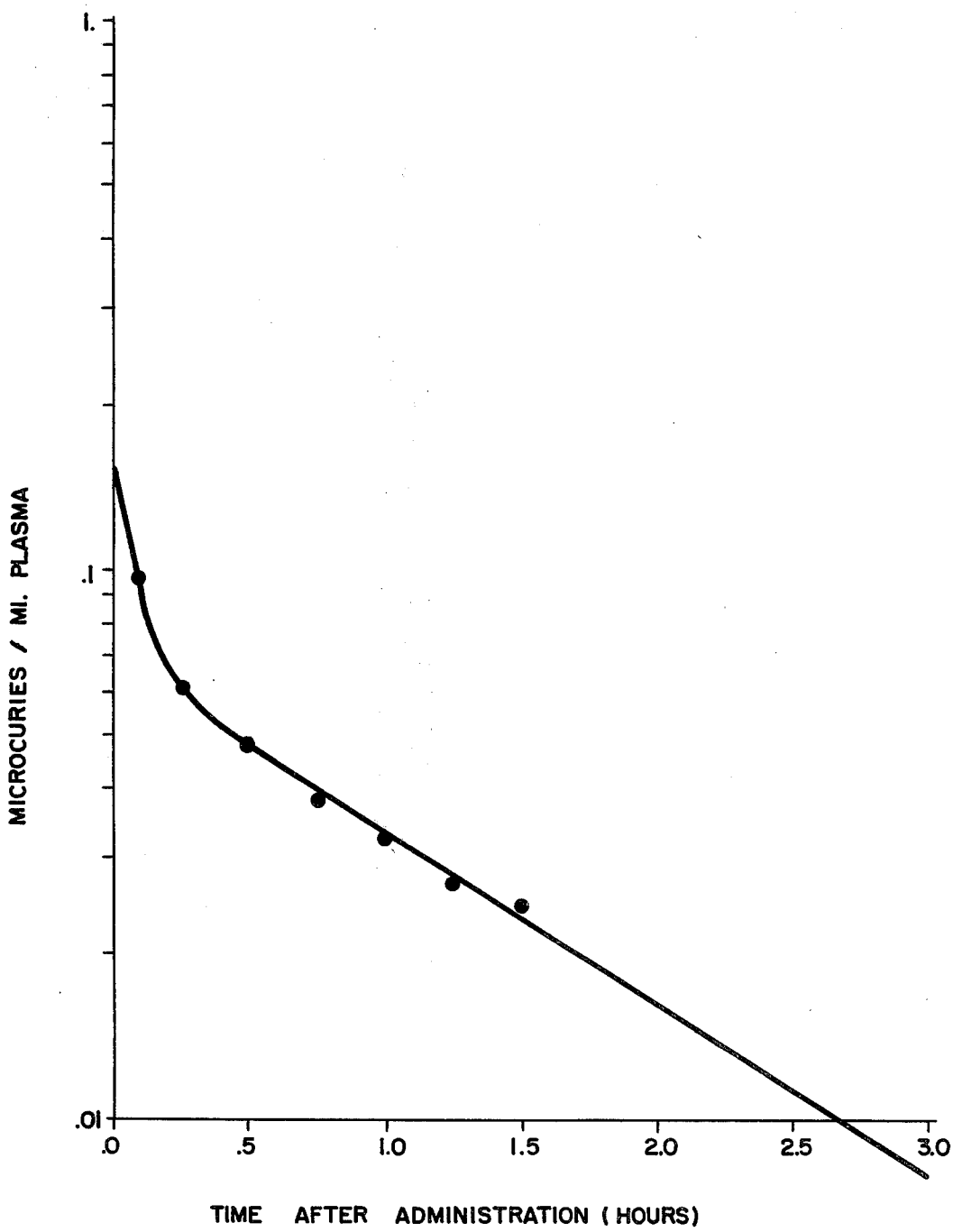
FIG. 2 is a semilog plot of the measured radioactivity of a complex of technetium-99m/tin and fructose 1,6-diphosphate per milliliter of plasma of a dog versus the time after intravenous administration of the complex to the dog.

Each of one male mongrel and three female beagle dogs was given at least one intravenous injection of a solution of the complex of technetium-99m and fructose 1,6-diphosphate or a solution of the complex of technetium-99m and fructose 6-phosphate. In each case about 0.5-2 milliliters of a solution of the complex having radioactivity of about 1-4 mCi and formed from 0.5-10 milligrams of complexing agent were administered. Four injections of solutions of the complex of technetium-99m and fructose 6-phosphate and 2 injections of solutions of the complex of technetium-99m and fructose 1,6-diphosphate were made. The dogs ranged in weight from 6 to 15 kilograms. Periodically blood samples were removed from the jugular vein of the dogs and collected in vacuum tubes containing the disodium salt of ethylenediamine tetracetic acid and the radioactivity of one milliliter samples of plasma were measured in a gamma spectrometer. The results of one typical case is presented in FIG. 2. FIG. 2 shows the radioactivity due to the presence in the plasma of the complex of technetium-99m and fructose 1,6-diphosphate versus the time in hours after administration to one of such dogs.

The gamma spectrometer employed was a Model 1185 Gamma Scintillation Spectrometer (Searle Analytic Inc., Des Plaines, Ill.). One milliliter samples of plasma or whole blood were analyzed for technetium-99m, and samples were counted for 1 minute. As determined by the computer, the curve in FIG. 2 and the five other corresponding curves (not shown) from the other tests with the dogs were the best fitting curves passing through the plots of experimentally measured radioactivities. In each case, the plots of experimentally measured radioactivities were found to follow a bi-exponential decay, indicating that the clearance of the complexes employed in the method of this invention, like $^{131}$I-o-iodohippurate, follow a two-compartment model for radiopharmaceutical agents.

The distributive phase for the clearance curve shown in FIG. 2 has a half time of 0.0565 hour. The elimination phase of the clearance curve shown in FIG. 2 has a half time of 0.947 hour. For the clearance curves of the four tests involving the complex of fructose 6-phosphate, the distributive phases have an average half time of 0.088 hour with a standard deviation of 0.023 hour, and the elimination phases have an average half time of 3.98 hours with a standard deviation of 3.29 hours. Elimination of a single obviously erroneous radioactivity measurement from one of these four clearance curves results in an improved average half time for the distributive phases of 0.072 hour with a standard deviation of 0.025 hour and for the elimination phases of 1.68 hours with a standard deviation of 0.72 hour. For the clearance curves of the two tests involving the complex of fructose 1,6-diphosphate, the distributive phases have an average half time of 0.063 hour with a standard deviation of 0.009 hour, and the elimination phases have an average half time of 1.34 hours with a standard deviation 0.23 hour. This illustrates that, after being distributed throughout the body, the complex of the method of the invention is cleared relatively quickly from the kidneys.

Furthermore, after being administered intravenously, the complexes of the method of this invention were rapidly distributed throughout the cardiovascular system. The kidneys selectively eliminated such complexes so that, for example, in the female dog, more than 60 percent of the administered radioactivity was excreted via the kidneys during the first 60 minutes. The rate at which the kidneys cleared the complexes from the vascular system was sufficiently rapid to permit evaluation of kidney function, permitting this rate of movement of the complexes to be a measure of renal function. With the rapid clearance of the complexes of the method of this invention from the cardiovascular system, there was a concomitant transfer of radioactivity to the urinary bladder, with virtually no hepatobiliary excretion.

The ratios of the measured radioactivity in the kidneys to the measured background radiation were about 10 to 1 and 4.5 to 1 at 4 minutes and 30 minutes, respectively, after administration of a complex of the method of this invention to a test dog, permitting clear imaging, or visualization, of the kidneys apart from their surroundings.

Figure 3:
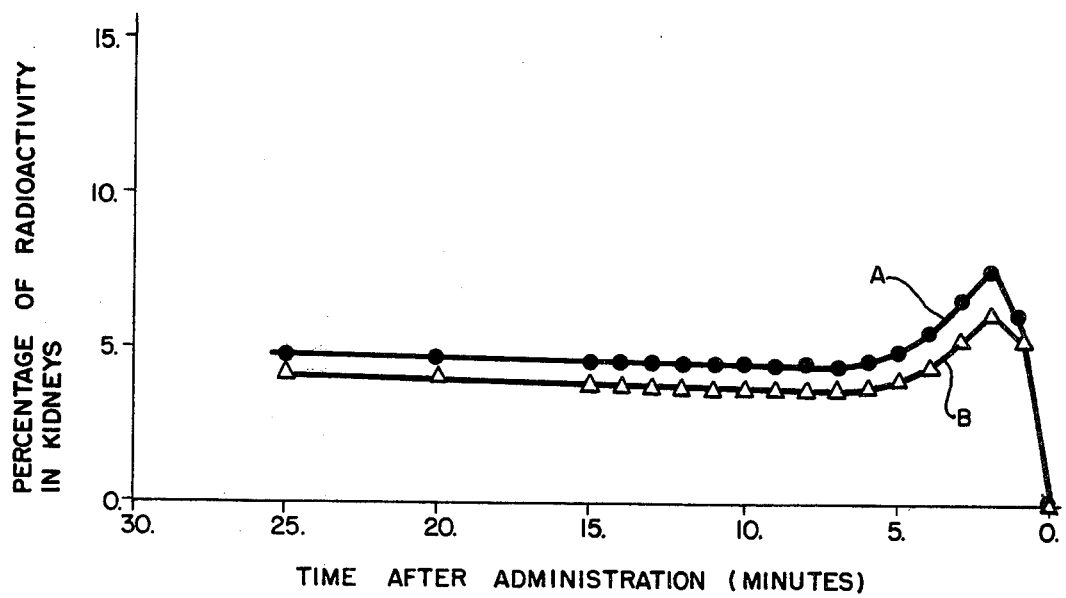
FIG. 3 contains plots of measured radioactivity found in the left and right kidneys of a monkey as a percentage of the total measured radioactivity of a complex of technetium-99m/tin and fructose 6-phosphate in the monkey versus time after administration of the complex to the monkey.
Figure 4:
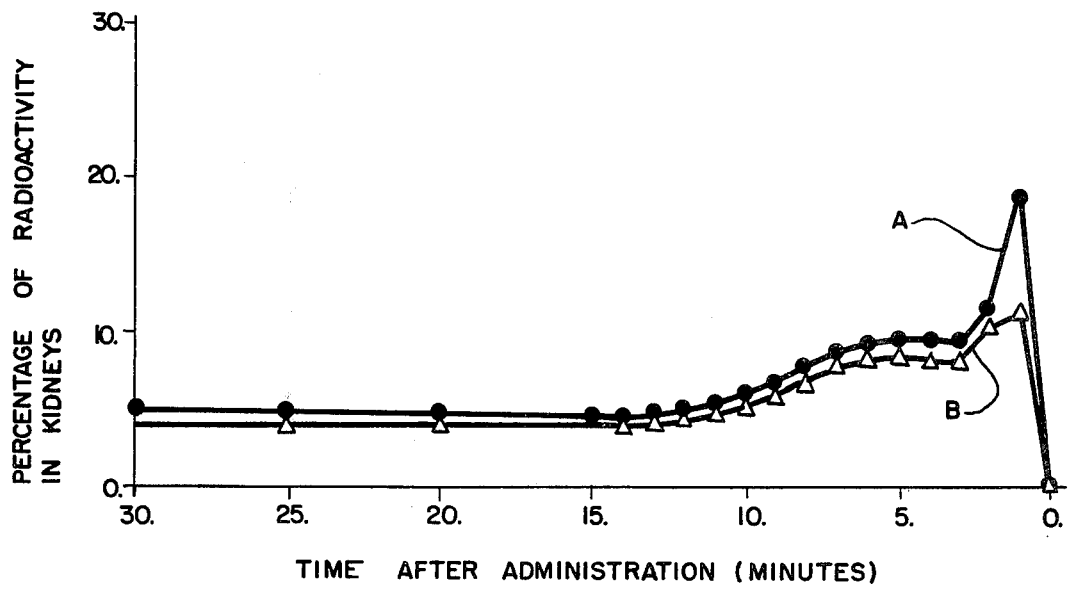
FIG. 4 contains plots of measured radioactivity found in the left and right kidneys of a dog as a percentage of the total measured radioactivity of a complex of technetium-99m/tin and fructose 6-phosphate in the dog versus time after administration of the complex to the dog.

Renograms showing the percentages of measured radioactivity in the left and right kidneys of a monkey and of a dog are shown in FIGS. 3 and 4, respectively. In each case, the test animal was administered a solution of a complex of technetium-99m and fructose 6-phosphate.

The suitability of the complexes of the method of this invention for monitoring the kidneys is contrasted with the complexes of technetium-99m with glucose 6-phosphate, D-ribose 5-phosphate, galactose 6-phosphate, 6-phosphogluconate and 3-phosphoglycerate which were found to be unsuitable when tested for the same utility.

These results are, of course, specified merely for the purposes of illustration and, accordingly, are not to be construed as either delimiting or exclusionary. Appropriate dosages in any given instance, of course, depend upon the species of mammal involved including its size and any individual idiosyncrasies which obtain.

The present invention will be more clearly understood from the following specific examples.

EXAMPLE 1

To a solution of 8.23 milligrams of fructose 1,6-diphosphate in 0.2 milliliter of water was added 0.2 milliliter of a solution of 0.16 milligram of stannous chloride dihydrate and about 0.8 milligram of 96 percent acetic acid in water. Immediately thereafter 2.5 milliliters of sodium $^{99m}$Tc-pertechnetate in normal saline, eluted from a commercial technetium-99m generator and having a radioactivity of 30.6 mCi, was added to the solution. The resulting solution had a pH of 5.40. At 16 minutes after the pertechnetate addition, the pH was adjusted to 6.02 using 0.1 N sodium hydroxide. Thin layer chromatographic analysis indicated that approximately 100 percent of the pertechnetate in the product was in the reduced form while only a trace amount of the pertechnetate was not reduced. Polyacrylamide gel column chromatographic analysis indicated that approximately 82 percent of the technetium was in the form of the complex of technetium-99m and fructose 1,6-diphosphate.

EXAMPLE 2

To a solution of 18.15 milligrams of fructose 6-phosphate in 0.2 milliliter of water was added 0.25 milligram of stannous chloride dihydrate and about 1 milligram of 96 percent acetic acid in water. Immediately thereafter 3.0 milliliters of sodium $^{99m}$Tc-pertechnetate in normal saline, eluted from a commercial technetium-99m generator and having a radioactivity of 25.7 mCi, was added to the solution. The resulting solution had a pH of 6.17. Thin layer chromatographic analysis indicated that at approximately 15 minutes after the pertechnetate addition, 95 percent of the pertechnetate in the product was in the reduced form, with only 5 percent of the pertechnetate being unreduced. Polyacrylamide gel column chromatographic analysis indicated that approximately 95 percent of the technetium was in the form of the complex of technetium-99m and fructose 6-phosphate.

From the above description it is apparent that the objects of the present invention have been achieved. While only certain embodiments have been set forth, alternative embodiments and various modifications, both of materials and methods, are apparent from the above description and examples to those skilled in the art. Such alternatives and modifications are considered equivalents and within the spirit and scope of the present invention.

We claim:

1. A method of externally monitoring the kidneys comprising administering intravenously to a patient a solution of a complex of technetium-99m and a compound having the formula

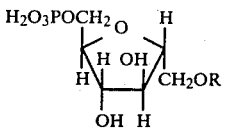

or a pharmaceutically acceptable salt thereof, wherein R is —H or —$PO_3H_2$, and monitoring radiographically the distribution of the complex in the patient and its clearance through the kidneys.

2. The method of claim 1 wherein R is —H.

3. The method of claim 1 wherein R is —$PO_3H_2$.

4. The method of claim 1 wherein a sodium salt of the complex is employed.

* * * * *